(12) United States Patent
Kaye et al.

(10) Patent No.: US 6,606,157 B1
(45) Date of Patent: Aug. 12, 2003

(54) DETECTION OF HAZARDOUS AIRBORNE FIBRES

(75) Inventors: Paul Henry Kaye, Hertfordshire (GB); Edward Hirst, Hertfordshire (GB)

(73) Assignee: University of Hertfordshire, Hertfordshire (GB)

( * ) Notice: Subject to any disclaimer, the term of this patent is extended or adjusted under 35 U.S.C. 154(b) by 0 days.

(21) Appl. No.: 09/254,824

(22) PCT Filed: Sep. 3, 1997

(86) PCT No.: PCT/GB97/02359

§ 371 (c)(1),
(2), (4) Date: Jun. 23, 2000

(87) PCT Pub. No.: WO98/11422

PCT Pub. Date: Mar. 19, 1998

(30) Foreign Application Priority Data

Sep. 14, 1996 (GB) ............................................. 9619242
Aug. 18, 1997 (GB) ............................................. 9717469

(51) Int. Cl.[7] ............................................. G01N 15/02
(52) U.S. Cl. .................... 356/336; 356/338; 356/343
(58) Field of Search ............................. 356/336, 337, 356/338, 339, 340, 341, 342, 343; 250/573, 574, 576

(56) References Cited

U.S. PATENT DOCUMENTS 5,105,093 A * 4/1992 Niwa ........................ 250/574
5,471,299 A * 11/1995 Kaye et al. ................. 356/336
5,530,551 A * 6/1996 Cantrall et al. ............. 356/394

FOREIGN PATENT DOCUMENTS

WO    WO 95/06238    * 3/1995

* cited by examiner

Primary Examiner—Hoa Q. Pham
(74) Attorney, Agent, or Firm—Robert D. Buyan; Stout, Uxa, Buyan & Mullins, LLP

(57) ABSTRACT

A fibre detector assembly comprising:
  (i) a scattering chamber body;
  (ii) means for drawing airborne particles through said body chamber, said means being adapted such the the particles tend to travel in single file with the longitudinal axis of particles with elongate shape substantially aligned with the direction of the air flow;
  (iii) means for illuminating the particle stream within the chamber body;
  (iv) an optical detector adapted to intercept and collect a portion of the light scattered by particles passing through the illuminating beam;
  (v) data processing means adapted to capture and process the signals from the optical detector;
  characterised in that the optical detector comprises a photodiode array consisting of a central opaque area surrounded by two or more annular rings of detector elements.

14 Claims, 6 Drawing Sheets

DETECTION OF HAZARDOUS AIRBORNE FIBRES

FIELD OF THE INVENTION

This invention describes a new instrument by which potentially hazardous individual airborne fibres, such as those of asbestos, may be detected in real-time within an ambient environment. The instrument uses a rapid analysis of the spatial laser scattering profile (i.e: the complex manner in which individual particles scatter laser light) recorded from individual airborne particles, as a means of classifying the particles in terms of their morphological characteristics. The instrument incorporates a dedicated detector array chip to record the spatial scattering profiles from individual particles at high throughput rates and dedicated electronic processing routines to establish the possible presence of hazardous fibres.

BACKGROUND TO THE INVENTION

The in situ detection of potentially hazardous respirable fibres has become a growing concern within industrialised countries as the health risks associated with these fibres have become more fully understood. The most commonly encountered hazardous fibres are of asbestos materials that, despite a wide-spread ban on their use for many years, are still present in vast quantities in public and commercial buildings and plants throughout the world. The most abundant asbestos mineral, Chrysotile (or white) asbestos, is present in over 95% of these installations. The second most commonly found variety is Crocidolite (or blue) asbestos, with Amosite (or brown) asbestos being a third but much rarer form. Crocidolite and Amosite belong to the amphibole class and are characterised by the fine, straight, needlelike fibres produced when the material is fragmented. Chrysotile asbestos belongs to the serpentine class of minerals and is characterised by a natural curvature in the fibres it produces. All three materials produce fibres that are capable of penetrating deep into the lung and that, because of their shape, become entrapped there. Crocidolite and Amosite fibres are known to be far more carcinogenic than those of Chrysotile asbestos, and although the exact reasons for this are still not confirmed, the half-life of the fibres in the lung (a function of the body's ability to chemically dissolve the fibres) is believed to play a major role since this may be measured in decades for amphibole fibres compared with months for Chrysotile fibres.

Airborne asbestos fibre is a significant health hazard. Peto et al (Peto, J., Hodgson, J. T., Matthews, F. E. and Jones, J. R. *The Lancet.* 345, 535–539, Mar. 4, 1995), for example, highlight the continuing increase in mesothelioma mortality in Britain as a result of respirable asbestos fibres generated during clearance operations or routine building maintenance work. The unambiguous confirmation of the presence of airborne asbestos fibres within an occupational environment can normally only be achieved by the use of filter cassette sampling of airborne particles followed by electron microscopy and, to determine chemical identity, a technique such as energy dispersive X-ray analysis. These processes are laborious and expensive to perform, and perhaps most importantly, provide results only many hours after the sample acquisition and possible personnel exposure has occurred. Several attempts have therefore been made to develop methods by which real-time or in-situ detection of airborne asbestos may be achieved. Rood et al [AP Rood, E J Walker and D Moore, "Construction of a portable fibre monitor measuring the differential light scattering from aligned fibres", in *Proceedings of the International Symposium: Clean Air at Work*, R H Brown, M Curtis, K J Saunders, and S Vandrendreissche, eds (*Royal Society of Chemistry*, London, 1992), pp 265–267] for example, have described a low cost portable fibre monitor developed at the UK Health & Safety Executive laboratories. This device is based on the differential light scattering produced by fibrous particles which are deposited electrostatically in uniform alignment onto a glass substrate. The device is capable of detecting fibrous particles but is not designed to detect individual particles, relying on the summation of scattering signals from a substantial number of deposited fibres in order to achieve a detectable signal. Rood states that the UK clearance limit for asbestos in buildings of 10 fibres per liter of air can be detected after about 300 minutes sampling time. This does not therefore constitute a real-time detection technique.

Another example is the comparatively widely used FAM-7400 Fibrous Aerosol Monitor (Mie Inc., Bedford, Mass.) developed originally by Lilienfeld et al. (Lilienfeld, P., Elterman, P., and Baron P. *A. Ind. Hyg. Assoc. J.* 40, 4, 270–282, 1979). This instrument draws air containing the airborne particles into a laser scattering chamber where the particles are carried along a horizontal glass tube coaxial with an illuminating laser beam. The particles remain in the beam for a comparatively long period, approximately 0.1 seconds, and many particles may be illuminated simultaneously. Around the glass tube is a quadruple electrode arrangement. By applying a time varying signal to the electrodes, the electric field within the tube causes electrically conducting fibres present in the air-flow to oscillate. The consequent cyclic variation in light scattered by the fibres to a single light detector at the side of the chamber is used to assess fibre concentration in the air. The FAM-7400 has several limitations (described in, for example 'Aerosol Measurement' by Willeke K. and Baron P. A., Van Nostrand Reinhold, 1993, pp 403–408): its sample volume flow rate through the laser beam is very low, resulting in comparatively long response times at low fibre concentrations (typically requiring 10 minutes to count 10 fibres at a concentration of 0.1 fibres/ml); it may classify as fibres non-fibrous particles which happen to oscillate in the applied electric field; since more than one fibre may be present in the beam at a given time, it can only estimate the number of fibres by the magnitude of the oscillation signal, and this requires some assumptions about the sizes of the fibres present; and it has reduced sensitivity for fibres which exhibit a natural curved morphology, such as the most common asbestos form, Chrysotile.

Spatial Laser Scattering Profiles

In theory, the detailed spatial intensity distribution of light scattered by individual particles (the scattering profile) contains information relating to inter alia the particle's size, its shape, and its orientation with respect to the incident illumination. The invention reported here is aimed at exploiting this fact with a view to discriminating, in real-time, individual respirable hazardous fibres, such as asbestos, from other particles within an ambient environment.

Most optical scattering instruments used for particle counting and/or sizing, rely on collecting the scattered light with a single discrete detector. Such instruments cannot provide information on particle shape, and indeed normally assume that all measured particles are spherical when ascribing a size value to them. When a small number of discrete detectors are used, each collecting light over a different solid angle within the sphere of scattering around the particle, some shape as well as size information is obtainable. This principle is embodied in a number of patented instruments which may be considered as prior art: ('Portable Particle Analysers'. Ludlow, I. K. and Kaye P H. European Patent EP 0 316 172, July 1992; 'Portable Particle Analysers Having Plural Detectors'. Kaye P H and Ludlow I K U.S. Pat. No. 5,043,591 August 1991; 'Particle Asymmetry Analyser having Sphericity Detectors'. Kaye, P. H. and Ludlow, I. K. U.S. Pat. No. 5,089,714. February 1992; 'Particle Asymmetry Analyser'. Ludlow, I. K. and Kaye, P. H. European Patent EP 0 316 171, September 1992; 'Analysis of Particle Characteristics'. Kaye, P. H., and Hirst, E. UK Patent GB 2278679B).

However, in order to extract more subtle information relating to particle morphology which may aid particle discrimination, the spatial intensity distribution of light scattered by the particle must be determined in more detail. If a particle is illuminated by a collimated light beam such as that from a laser, it will scatter light in all directions. FIG. 1 shows examples of forward scattering (i.e: below 35° to the incident beam direction) recorded from various types of particle. These images were recorded using a laser scattering instrument fitted with a high-speed intensified charge-coupled-device (CCD) camera to record the light scatter data. In the instrument, the airborne particles are carried through an illuminating beam in single file by a laminar flow delivery system. The particles were illuminated by a 5-mW, 670 nm diode laser. This delivery system imposes aerodynamic forces upon the particles which cause fibrous or elongated particles to align preferentially with their long axis parallel to the flow, ie: orthogonally to the laser beam. The camera captures the distribution of light scattered by the particle throughout the angular range 5° to 35° to the illuminating beam direction.

The scattering profile examples given in FIG. 1 are recorded from typical background outdoor air (which contains a wide variation of particle types including droplets, irregular cubic particles, and occasional fibrous particles); from Crocidolite (or blue) asbestos; and from Chrysotile (or white) asbestos. Because elongated particles tend to align with the airflow (which for the examples shown was vertical), the fibres thus tend to traverse the laser beam vertically with the consequence that the scattering is predominantly in the horizontal plane, as illustrated in the Crocidolite and Chrysotile examples of FIG. 1. The data show in FIG. 1 illustrate the way in which scattering profiles, since they relate closely to the morphology or shape of the particles which produced them, may be used to discriminate between particle species, such as varieties of asbestos fibre, which exhibit very characteristic morphological features.

Typical scattering profiles from background particles, shown in the top row of FIG. 1, produce very variable profiles with few interpretable features since the particles which produced them are generally of irregular compact form. In contrast, the profiles produced by Crocidolite fibres, shown in the middle row, exhibit clearly discernible features: the profiles are generally of the form of a horizontal bar of scattering passing through the centre of the profile. The near horizontal form is as a result of the substantially vertical orientation of the fibre in the laser beam. The scattering is very localized as a result of the characteristic needle-like shape of the Crocidolite fibres, with virtually all the scattered light lying within a substantially horizontal bar. The total amount of scattered light may be related to a first order to the size (volume) of the scattering fibre, and the thickness of the scattering bar to the length-to-thickness aspect ratio of the fibre (higher aspect ratio fibres produce thinner scattering bars). It is therefore possible from each profile to estimate both the size and shape of the fibre which produced it, and this information is of great importance in the monitoring of hazardous respirable fibres such as asbestos since these parameters are known to significantly influence the degree of threat posed by the fibres upon inhalation.

Additionally, the bottom row of FIG. 1 illustrates the scattering from Chrysotile asbestos fibres which, being normally curved, cause the scattering profiles to assume a characteristic 'bow-tie' appearance. Here the scattering is still predominantly horizontal but the differing inclinations of incremental sections of fibre length to the incident illumination cause the fine divergent structure shown. The examples given in FIG. 1 illustrate the differences in the forms of the scattering profiles which exist for different particle morphologies, and indicate that this type of scattering profile offers the prospect of (i) discriminating asbestos-like fibres from background airborne particulates, (ii) the possible discrimination between serpentine (curved) and amphibole (straight) asbestos fibres, the latter being of higher carcinogenicity, and (iii) an estimate of the fibre size and shape and therefore potential threat posed by inhalation.

SUMMARY OF THE INVENTION

According to a first aspect of the present invention there is provided a fibre detector assembly comprising:
(i) a scattering chamber body;
(ii) means for drawing airborne particles through said body chamber, said means being adapted such the the particles tend to travel in single file with the longitudinal axis of particles with elongate shape substantially aligned with the direction of the air flow;
(iii) means for illuminating the particle stream within the chamber body;
(iv) an optical detector adapted to intercept and collect a portion of the light scattered by particles passing through the illuminating beam;
(v) data processing means adapted to capture and process the signals from the optical detector;
characterised in that the optical detector comprises a photodiode array consisting of a central opaque area surrounded by two or more annular rings of detector elements.

This arrangement provides for the real-time measurement of hazardous particles in a working environment. The special detector array makes this possible for the first time.

Preferably the detector array comprises three concentric annular rings of detector elements. The concentric array arrangement means facilitates the gathering of scattering data in an easily manageable form.

In a further preferred embodiment the first or innermost annular ring comprises a single detector and the second and subsequent annular rings each consist of a plurality of detector elements.

Preferably the radial interfaces between detector elements or segments in adjacent annular rings are out of phase. This then minimizes the possibility of fine fibre scattering from elongated fibres lying entirely along the 'dead-zones' between adjacent detector elements in both the A and B segmented rings, and the commensurate possibility that fibre detection could be compromised.

In a particularly preferred embodiment the optical detector comprises three annular rings and the two outermost rings are divided into 16 segments or elements.

Preferably the annular rings of detector elements in the optical detector are substantially circular. A circular arrangement with radial segments is an efficient arrangement for detecting and gathering scattered light.

Preferably the data processing means incorporates a pattern classifier, which preferably comprises a neural network.

Preferably the neural network is a radial basis function neural network.

According to a second aspect of the invention there is provided an optical detector suitable for use in a fibre detector assembly of the type in question comprising a photodiode array consisting of a central opaque area surrounded by two or more annular rings of detector elements.

Preferably the first or innermost annular ring comprises a single detector and the second and subsequent annular rings each consist of a plurality of detector elements.

In a preferred embodiment the radial interfaces between detector elements or segments in adjacent annular rings are out of phase.

In a particularly preferred embodiment the optical detector comprises 3 annular rings and the two outermost rings are divided into 16 segments or elements.

Preferably the annular rings of detector elements are substantially circular.

For the avoidance of doubt this invention includes the optical detector as an entity in its own right for installation into existing fibre detectors. The invention also includes a complete fibre detector and a method of detecting hazardous fibres using said detectors.

DESCRIPTION OF THE DRAWINGS

The invention will be further described, by way of example only, with reference to the accompanying drawings in which.

DESCRIPTION OF THE PREFERRED EMBODIMENTS

The invention will now be described by way of example only. These examples represent the best ways know to the applicant of putting the invention into practice but they are not the only ways this can be achieved.

According to a first aspect the invention comprises a fibre detector assembly comprising a scattering chamber body, a means of drawing ambient airborne particles through this body in a constrained manner such that the particles travel in essentially single-file and are subject to aerodynamic or other forces which are able to preferentially orientate with the flow those particles which exhibit elongated morphology or shape, a means (usually a laser) of illuminating this particle flow orthogonally in such a way that in normal circumstances particles pass through the illuminating beam singly, a means of intercepting and collecting the distribution of light scattered by each particle and directing this onto an optical detector without loss of information relating to the spatial distribution of the intensity of light scattered by the particle, a means within the optical detector of measuring the broad pattern features contained within the scattered light distribution, and a means of electronically processing this information in such a way as to characterise and classify the particle morphology which produced it, with particular emphasis on the detection and characterisation of hazardous respirable fibres such as those of asbestos.

Figure 2:
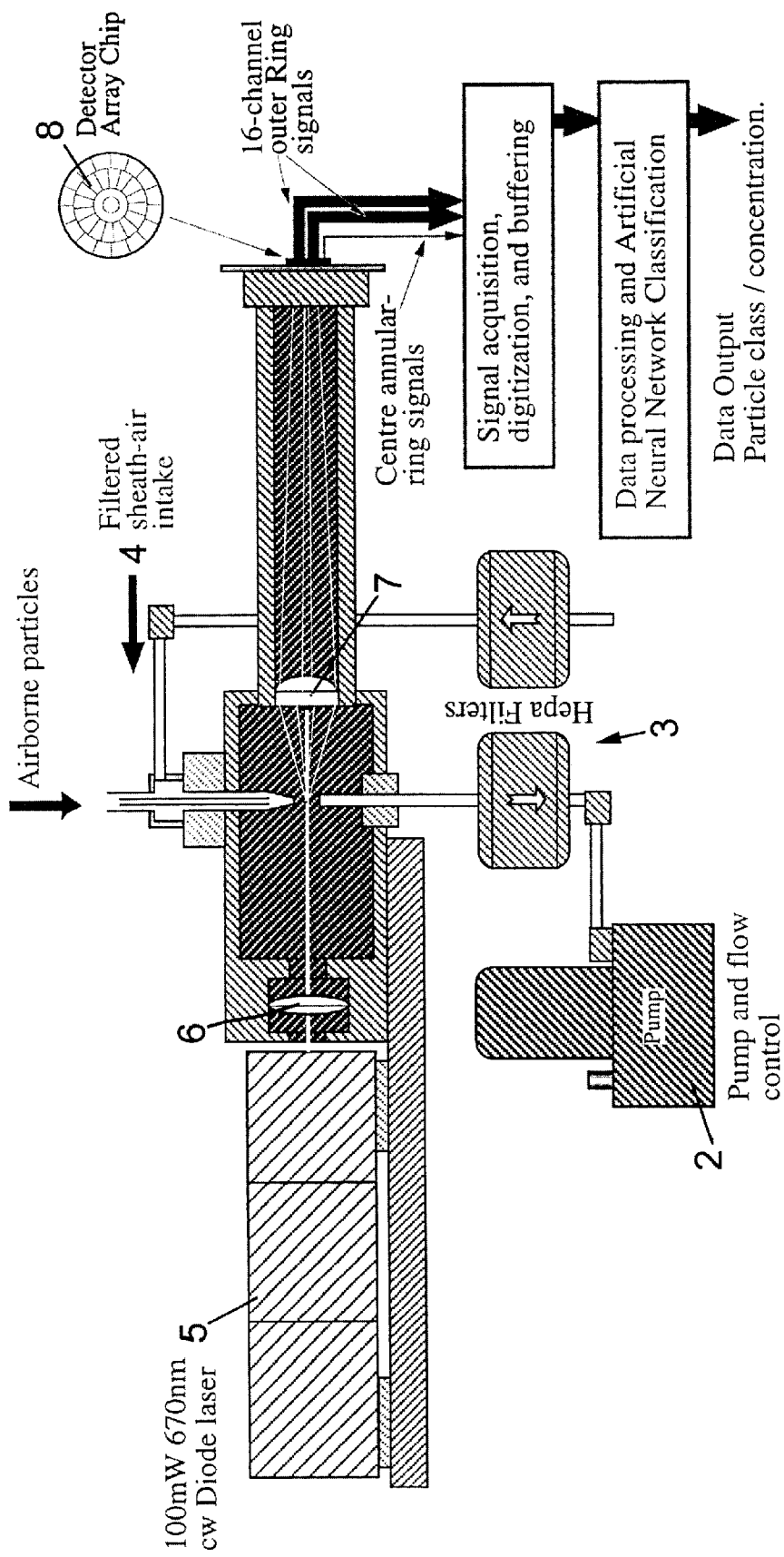
FIG. 2 illustrates a fibre detector system according to the present invention.

A preferred embodiment of the invention is shown in FIG. 2. Airborne particles are drawn in through a scattering chamber by a pump 2. Particles are prevented from contaminating the pump by a filter 3. The sample airflow is ensheathed by clean filtered air 4 with the consequence that the sample airflow is narrowed to the point where the airborne particles are constrained to move essentially in single file. The sample airflow crosses the beam from a light source 5, the preferred embodiment being a diode laser although other light sources can be used. Optics 6 collimate and appropriately shape the beam to an ellipsoidal shape of approximately 2 mm width and 0.1 mm depth at the intersection with the particle flow. The intersection of the airflow and the laser beam defines the scattering volume. Individual particles in the sample air traverse the laser beam and produce pulses of scattered light. This light is incident upon a lens system 7 which images light scattered by the particle between angles of approximately 4° and 30° to the primary beam axis onto a custom detector chip 8 which records the scattered light distribution for each particle traversing the laser beam.

The new fibre characterisation instrument incorporates the selected detector geometry as a custom photodiode array chip. The chip has a diameter of 11 mm and is mounted into a commercial pin grid-array package with no covering window. The laser output is linearly polarised in the plane of the diagram. The beam cross section at the intersection with the sample airflow is of ellipsoidal shape, approximately 2 mm in width and 0.1 mm in depth, leading to a particle transit time through the beam of ~5 $\mu$s. Sample airflow through the device is set to be 1 l/min. Because particle trajectories through the beam could take place anywhere within the horizontal cross-sectional area of the sample air column (approximately 1 mm in diameter), the scattered light capture optics are designed to ensure that such particle trajectory variations do not cause significant translation of the scattering profile image on the detector array. The centre detector ring C receives light scattered between 4° and 10° to the primary beam axis; the second and third rings, B and A, receive light scattered between 10° and 18° and 18° and 28°, respectively.

Figure 7:
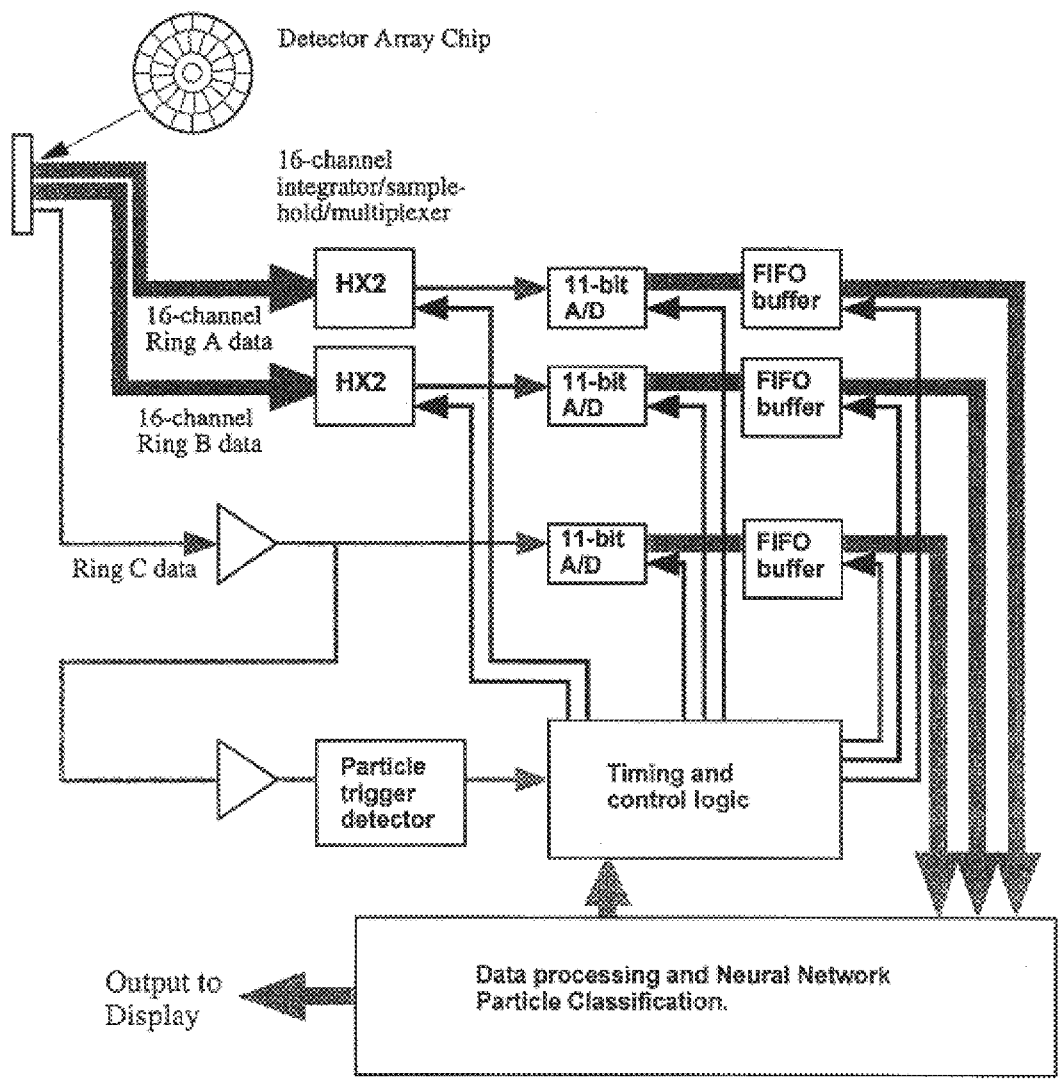
FIG. 7 shows a schematic diagram of the acquisition and digitisation process for light-scattering signals derived from the detector array chip shown in FIG. 3.

The operation of the signal acquisition, digitisation and buffering electronics is shown schematically in FIG. 7. When a particle enters the laser beam the signal received from the central annular ring C begins to rise. This rise is selected by a particle trigger detection circuit that initiates data acquisition from the other 32 detector elements. This acquisition is achieved by two dedicated application-specific integrated circuit chips, labelled HX2 in FIG. 7. These chips are manufactured by Rutherford Appleton Laboratories, Didcot, UK. Each HX2 chip contains 16 parallel integrators that integrate the signals from the individual detector elements for the duration of the particle transit through the beam. The chips then hold these analogue signal values and serially multiplex them out to analogue-to-digital converters. FIFO (first in first out) buffers subsequently store the digital data, 33 values per particle, before transferring them at an optimal rate to the neural network data processing system (based on dual Motorola 68040 processors) for particle classification.

Figure 1:
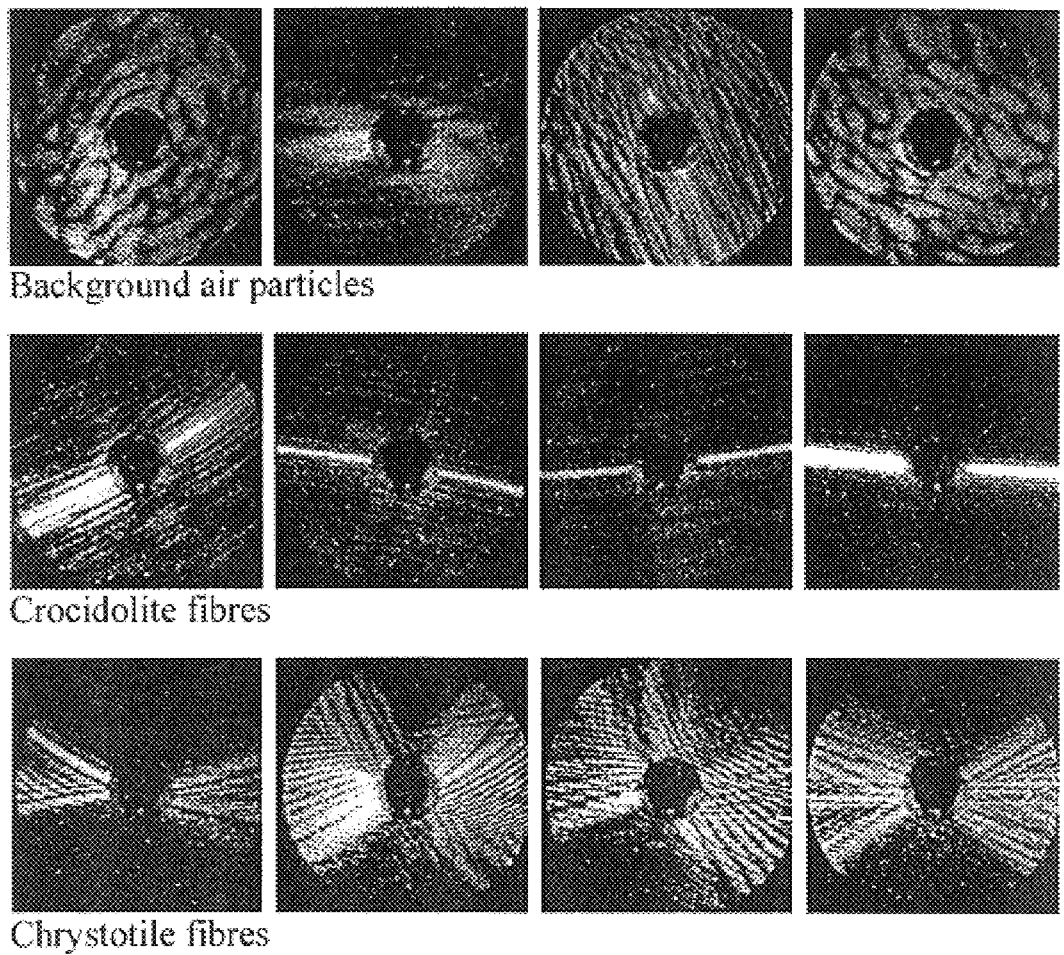
FIG. 1 illustrates typical scattering profiles recorded from individual particles or fibres.

In order to make use of the particle morphology information contained within the scattering distributions of the type shown in FIG. 1, an instrument must satisfy the conflicting requirements of (a) determining the profiles with sufficient resolution to allow recognition of the characteristic pattern features, and (b) not producing such highly detailed information that the rapid analysis of individual particles and hence the instrument's application in a real-time monitoring scenario is precluded because of excessive data processing requirements. The latter consideration may be quantified by the following example: The statutory UK limit for asbestos fibres escaping the containment area during clearance operations is 10 fibres per liter of air. In order to detect these fibres in 'real-time', taken here to be typically 1 minute, the instrument must examine all the particles within 1 liter of air within a period of 1 minute. In a typical clearance operation there may be 100,000 respirable dust and other particles per liter of air, and the instrument must therefore be capable of analysing in excess of 1500 particles per second, or one particle in a fraction of a millisecond. In reality, because particle transits through the instrument occur randomly, the true processing time required to avoid a particle being 'missed' during processing data from the previous particle is less than 0.1 milliseconds. The instrument should also have the attributes of delivering the particles singly through the illuminating beam, and of inducing preferential alignment of elongated particles so as to aid interpretation of the scattering data. The current invention is capable of achieving these performance criteria.

Figure 3:
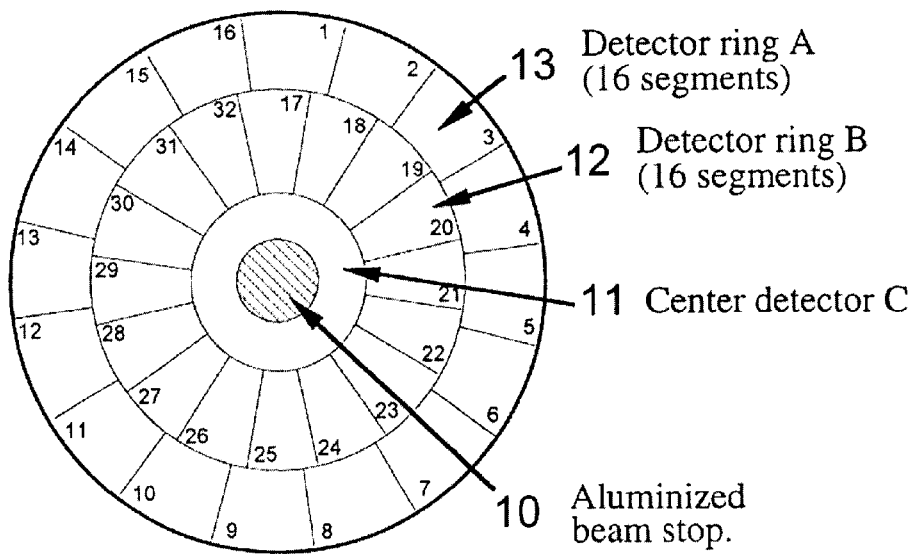
FIG. 3 illustrates a 33 element detector array chip.

A preferred embodiment of the detector being a second aspect of the invention is shown in FIG. 3. The detector would be typically a photodiode array manufactured upon a single silicon wafer for reasons of compactness, robustness, dimensional accuracy, and the ability to define light-sensitive areas of any desired shape with minimal 'dead-zones' between adjacent detector elements. The detector comprises a central circular area 10 surrounded by three annular rings, 11, 12, and 13. The central circular area 10 is opaque to incident light so as to act as a beam-stop for the illuminating beam of light. The first annular ring 11 is continuous and as such will receive scattered light no matter what the orientation of the particle in the beam (the output from this detector ring is used for particle size determination). The second ring 12 is divided into 16 segments, each giving an output signal proportional to the light falling on that segment 3. The third ring 13 is similarly divided into 16 segments, but the interfaces between adjacent segments are out of phase with those of the second ring 12. This phase difference eliminates the possibility of the fine scattering from an elongated fibre being undetected in the event that it falls along the 'dead-zone' between detector segments. In the event that the scattering falls along the 'dead-zone' of the second ring, it would invariably fall within the active area of a segment within the third ring. The second and third rings provide the spatial analysis of the scattered light distribution falling on the detector.

The detector shown in FIG. 3 consists of three substantially circular annular rings segmented as required in a radial fashion. But this is not the only arrangement which is possible. Concentric ellipses, squares or rectangles are equally possible. Furthermore, one or more additional rings of detector elements can be added if required. It is, however, preferred that the radial interfaces between the detector elements or segments in adjacent rings are off-set or out of phase with each other for the reasons stated.

Figure 4:
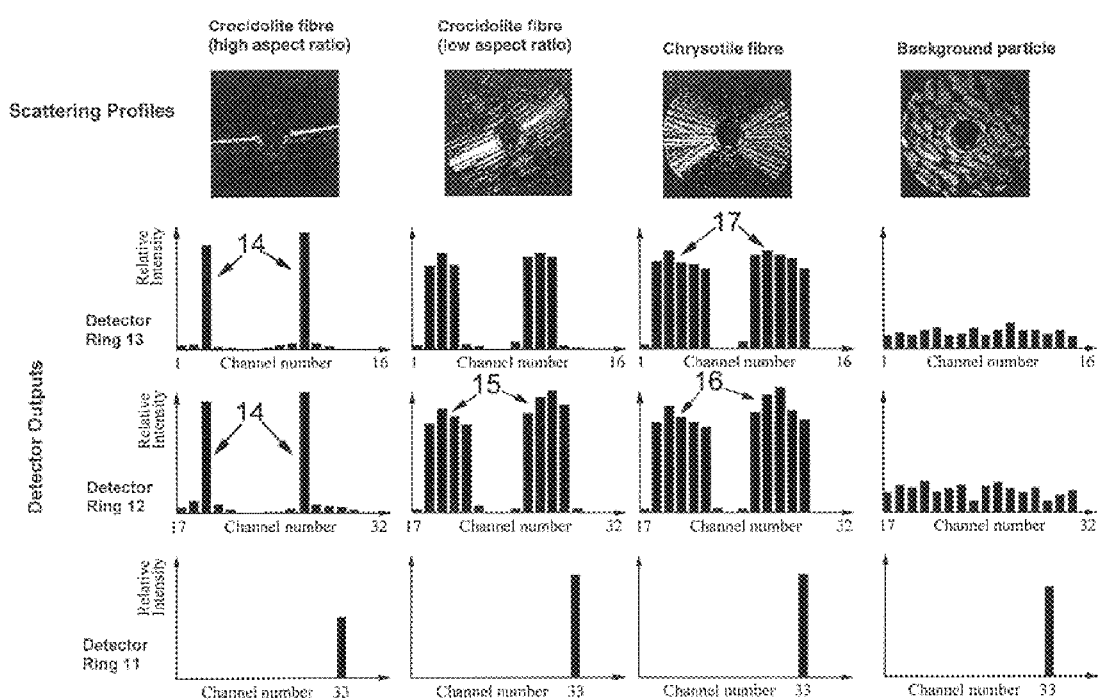
FIG. 4 illustrates typical responses of a fibre detector assembly according to the present invention to different particle types.

For each particle passing through the illuminating beam therefore, the detector produces 33 output values. Analysis of these values yields the required characterisation of the particle and the identification and classification of fibrous particles. FIG. 4 illustrates the typical output values of the detector for four types of particle: (i) a high-aspect ratio Crocidolite fibre with a consequently thin scattering bar; (ii) a low-aspect ratio Crocidolite fibre with a thicker scattering bar; (iii) a Chrysotile fibre giving a characteristic 'bow-tie' form to the scattering; and (iv) a background air particle. With the high-aspect ratio Crocidolite fibre scattering, the second and third detector rings, 12 and 13, each exhibit two distinct narrow peaks 14 in accordance with the narrow scattering distribution, as shown in FIG. 4, whilst the first ring 11 yields a single value proportional to the fibre size. With the low-aspect ratio Crocidolite fibre scattering, the second detector ring 12 exhibits two peaks 15 of greater width than for the high-aspect ratio case, whilst the third ring 13 similarly produces two peaks though these are narrower than those in the second ring 12 in accordance with the number of segments within each ring which are illuminated by the scattered light. Again, the first ring 11 yields a single value proportional to the fibre size. The Chrysotile fibre produces a result which can be distinguished from that of the low aspect-ratio Crocidolite fibre by virtue of the fact that the widths of the two peaks 16 in the second ring 12 are equal to the widths of the two peaks 17 in the third ring 13 rather than being greater as in the former case. The background particle results in no discernible peaks in either the second or third detector rings. The detector outputs therefore contain information which can be used to discriminate fibrous particles from non-fibrous particles, to discriminate straight from curved fibres, to assess fibre aspect ratio, and to assess overall fibre size.

The data from the detector must be processed rapidly to yield particle classification as discussed earlier in order to satisfy the requirement for real-time instrument operation. This processing is carried out by electronic means using one of a number of established mathematical classification methods including Normal Distribution Method, Linear Discriminant Method, or K-Nearest Neighbours Method (all described in, for example, 'Pattern Classification and Scene Analysis' by Duda R, O. and Hart P. E., Wiley Interscience 1973), or by using an artificial neural network pattern recognition method (described in, for example, 'Neural Networks for Pattern Recognition' by Bishop C. M., Oxford Univ. Press 1995).

The Radial Basis Function or RBF network is arguably one of the simplest forms of an artificial neural network. It is based on the use of training data, in our case these being example sets of 100 scattering patterns from each of the particle classes that we wish to discriminate. The training data result in defined regions of mathematical hyperspace corresponding to the chosen classes. When new data (expressed as an input vector) derived from an unknown particle are input to the network, the network evaluates the distance between this input vector and its predefined class data regions and indicates to which class the unknown particle corresponds most closely.

Figure 5:
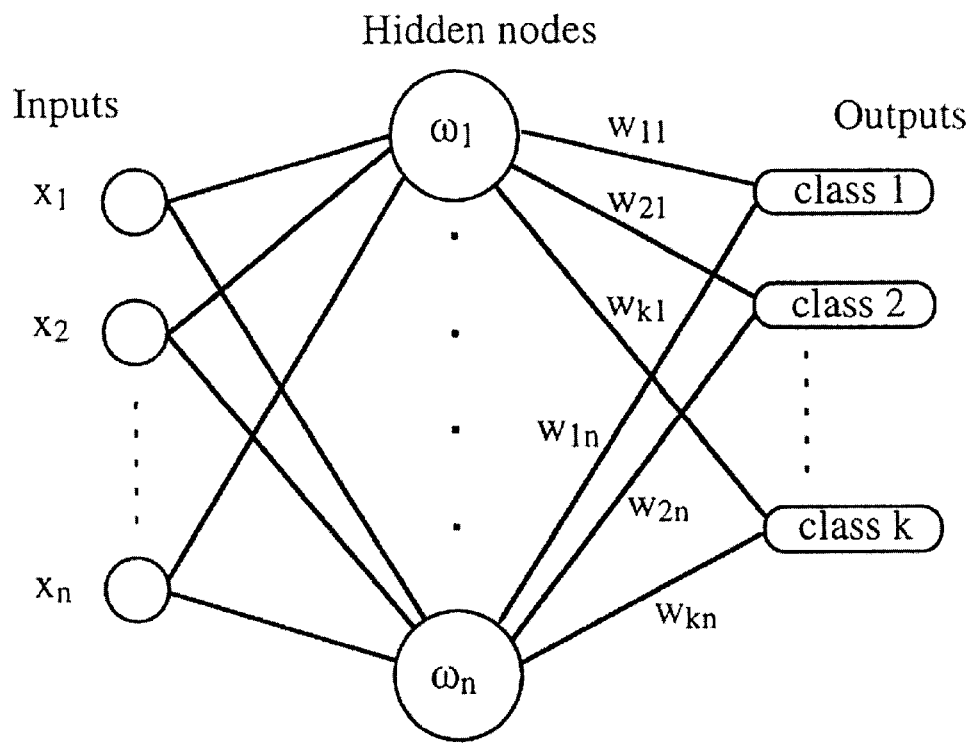
FIG. 5 shows a schematic illustration of the basic elements of an RBF neural network.

The RBF network has an architecture consisting of only one hidden layer, as illustrated in FIG. 5. In the present case, the inputs, labelled $\chi_1$ to $\chi_n$ represent the values of the light-scattering data from either the A or B detector ring; these are processed independently through the network so as to allow a voting on the classification outcome. Only if both processes resulted in the same as classification for a particle (judged as that having the highest linear summation output value) is the particle ascribed to that class (shown as class 1, class 2, etc., in FIG. 5). If there was a discrepancy in classification results from the two detector rings, the particle is classified into the lower of the two classes.

The hidden nodes $\omega_1$ to $\omega_n$ are RBF's that take the form $$\omega_i(\|\chi - \chi_i\|), \quad (1)$$

where $\omega_i(\cdot)$ is a non-linear function of the distance between the input vector $\chi$ (based on the detector ring values for the unknown particle) and the ith centre vector $\chi_i$ marking the hyperspace region corresponding to each prescribed class of particle). The network output vector class is simply the linear summation of the weighted basis functions $$class_j = \sum_{i=1}^{n} w_{ji}\omega_i(\|\chi - \chi_i\|), \quad j = 1, 2, \ldots, k, \quad (2)$$

the weights for each class $\omega_{11}, \omega_{21}, \ldots$ to $\omega_{kn}$ having been established by the training data. In this case, the RBF's were chosen to be Gaussian, a commonly used approach and one that gave good classification results. The functions were of the form $$\omega_i(\|\chi - \chi_i\|) = \exp\left(\frac{\|\chi - \chi_i\|^2}{d^2}\right) \quad (3)$$

where d is a constant bandwidth parameter.

Figure 6:
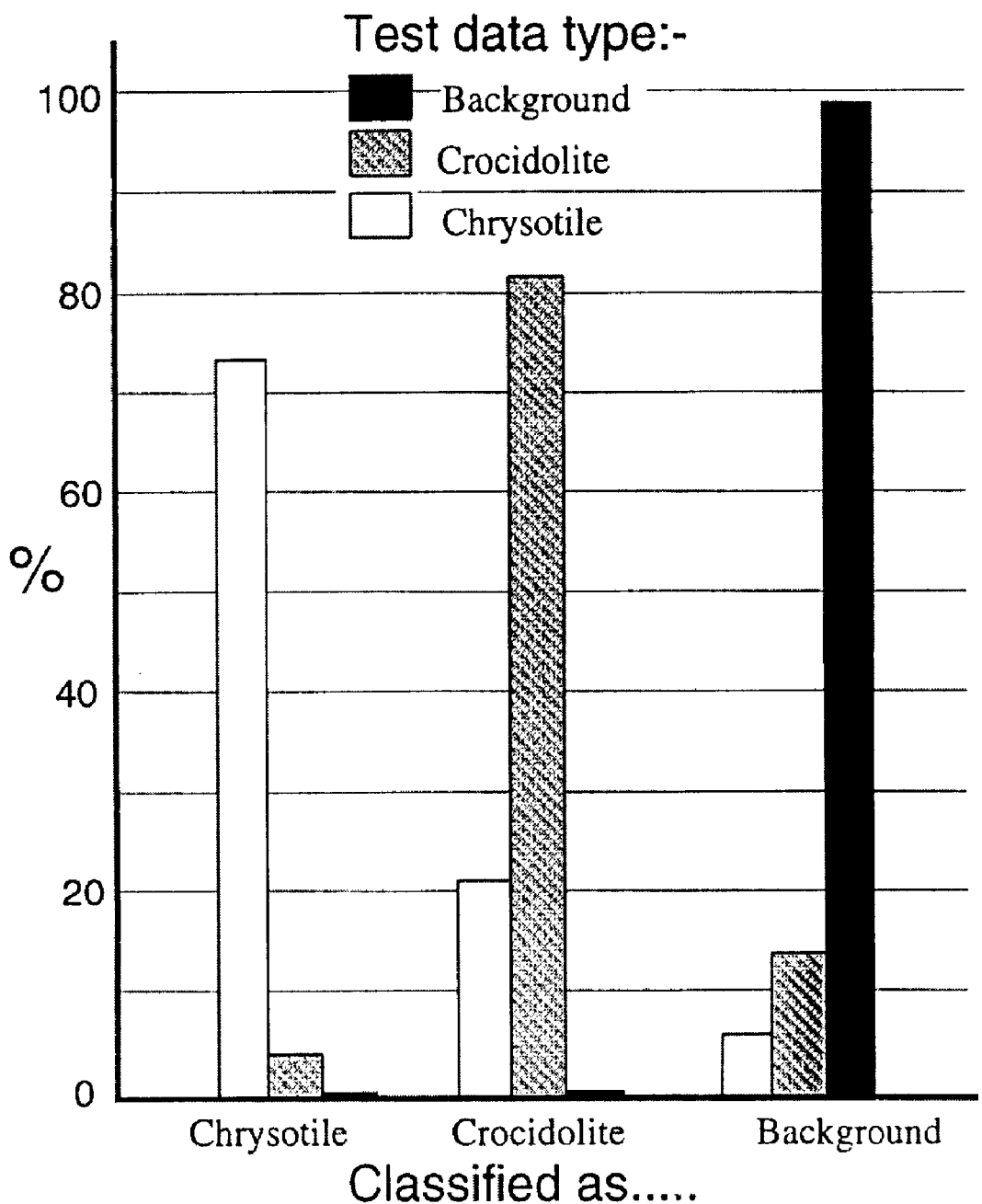
FIG. 6 shows a graphical representation of the simulated performance of the detector configuration shown in FIG. 3 and the RBF neural network in terms of classifying particles from known aerosols.

FIG. 6 summarises the simulated classification performance of the preferred detector geometry and the RBF analysis method. Some 10,000 examples of scattering profiles recorded from known aerosols of each of the three chosen particle types (Chrysotile, Crocidolite, and background) were processed and classified into their respective classes. Ideally, 100% of each input test data type should be classified into its correct particle class. In practice, over 99% of background particles were classified correctly as background, with 0.1% being misclassified as Chrysotile particles and 0.6% misclassified as Crocidolite. These misclassification figures are as result of nonasbestos fibres within the background sample producing scattering profiles sufficiently similar to the extremes of the Chrysotile or Crocidolite classes that they were classified as such. They therefore represent a threshold level against which actual fibre concentration measurements must be compared. Similarly, over 80% of Crocidolite and 70% of Chrysotile particles were classified correctly. The misclassification of the remainder of these particles into the background class is inevitable when this laser scattering technique is used because some Crocidolite or chrysolite particles are aerosolised as irregular clumps of fibre aggregates that do not produce characteristic fibre scattering. The consequence will be the underestimation of the true asbestos fibre concentration by some small margin, although this parallels the decision processes that occur during the standard phase contrast light microscope filter sample counting technique.

To assess the performance of the machine neural network against results achieved by manual classification, experiments were carried out using aerosols containing mixed particle types. For each aerosol, data relating to 3000 particles were classified, first by visual inspection by a trained volunteer and second by use of the RBF neural network classifier. The data were of the form similar to that shown in FIG. 4. Because these mixed aerosols contained Crocidolite, Chrysotile, and background particles and it was known that some overlap in the scattering characteristics of these materials was inevitable (as illustrated in FIG. 6), the classifications used were high-risk fibres (those that displayed predominantly Crocidolite-like scattering features), medium-risk fibres (those that displayed predominantly Chrysotile-like scattering features), and other particles. Table 1 summarises the results for one such mixed aerosol, illustrating the close similarity in classification performance between machine and manual classifications:—the significant difference being that the manual classification required several hours (similar to that required for phase contrast light microscope fibre counting on filters), whereas the machine classification required only seconds.

TABLE 1

Summary of the Classification of Scattering Profile Data from a Mixed Aerosol Containing Crocidolite, Chrsotile, and Background Particles

| Particle Class | Manual Classification (%) | RBF Neural Network Classification (%) |
|---|---|---|
| High-risk fibres | 4.4 | 4.3 |
| Medium-risk fibres | 15.4 | 14.3 |
| Other particles | 80.2 | 81.4 |

The classification was achieved both by visual inspection of graphical data (similar to those shown in FIG. 4) and by RBF neural network analysis. High-risk fibres are those that display Crocidolite-like scattering profiles; medium-risk fibres are those that display Chrysotile-like scattering.

A further preferred method of analysis using a Linear Discriminant technique is as follows: For each desired class of particle (e.g.: high-aspect ratio fibres, low-aspect ratio fibres, curved fibres, background particles, etc.), fifty examples of typical scattering data as shown in FIG. 4 are manually selected to become the 'templates' for the desired classes. The data from the second ring 12 is processed independently from that of the third ring 13 so as to improve classification performance, as described below. For each particle data, the Fourier Transform (FT) of the sixteen data outputs of the second detector ring 12 is computed. This Fourier Transform removes pattern rotational dependencies in the profile information which could otherwise make classification more difficult. The FT data for each particle in the set of fifty particles of a given class is then used to establish in hyperspace the distribution of points describing that class (see Duda and Hart for detailed explanation). This is repeated for each desired class of particle.

When data is obtained from an unknown particle, the FT is computed for the second detector ring 12 outputs and a Linear Discriminant function is then computed to assess the probability of that particle belonging to any of the classes for which 'templates' exist. The particle is ascribed the class which it most closely fits. A similar process is performed with the output data arising from the third detector ring 13 and a matching class is determined using that data also. Only if the same class is indicated by the data from the second detector ring 12 and the third detector ring 13 is the particle finally ascribed to that class. If the data from the two rings yields different classes, the particle is classified as a 'background air' particle. This voting method enhances the accuracy of the particle classification and reduces the possibility of falsely classifying innocuous background air particles as a hazardous respirable fibres.

Finally, the particle classification data is collated with that of all other particles sampled within that time period, typically 5 seconds, and the cumulative result displayed to the user as a particle class concentration histogram. The histogram is thus updated at 5 second intervals to provide a real-time indication of the presence or otherwise of hazardous respirable fibres.

The format of the optical detector and the method of handling data from the array of sensors within the detector are key features of this invention. They provide, for the first time, a detector array and thus a fibre detector capable of detecting hazardous fibres in the workplace in a useful timescale that will alert operatives to the presence of a hazard as it arises.

For the avoidance of doubt, this application is intended to encompass an optical detector as described above as a discrete entity, as well as a compete detector assembly containing a detector of the type in question. Such an optical detector could be substituted in a detector assembly of the prior art type to increase its performance. Such a detector may also have other application in areas where there is a need to characterise particle species in terms of size and/or morphological parameters. These include environmental monitoring of stack emissions, vehicle exhausts, various airborne biological particles such as pollen, fungal spores, or bacteria (in the indoor as well as outdoor environments); the characterisation of powder products such as ceramic powders, paint pigments, or powdered foodstuffs. Other areas may include liquid-borne particle characterisation, including the analysis of: the presence of solid, liquid, or air bubbles carried in suspension in hydraulic liquids (which can compromise the efficiency of the hydraulic system and, in some cases may be a precursor of catastrophic system mechanical failure, as in helicopter gearboxes and control systems); the presence of biological organisms in water, especially bacterial regrowth in the outputs of water processing plants supporting domestic and industrial consumption; the presence of particulates in highly purified liquids, such as those for use in medical intravenous applications or in industrial processing where particulates are to be avoided (as in microelectronics or pharmaceutical manufacture); the presence of particles of rust or other solids and droplets of water carried in fuel (such as petroleum based aviation fuel, petrol, diesel, etc.), which can cause engine misfire or eventual failure. This list is not exhaustive but is indicative of the range of application areas where the invention could be usefully employed for particle characterisation.

What is claimed is:

1. A detector assembly suitable for detecting fibres said detector assembly comprising:
    (i) a scattering chamber body;
    (ii) means for drawing airborne particles through said body chamber, said means being adapted such that the particles tend to travel in single file with the longitudinal axis of particles with elongate shape substantially aligned with the direction of the air flow;
    (iii) an illuminator for illuminating the particle stream within the chamber body;
    (iv) an optical detector adapted to intercept and collect a portion of the light scattered by each particle passing through the illuminating beam wherein the optical detector comprises a photodiode array consisting of a central opaque area surrounded by at least two annular rings of detector elements, at least one of said annular rings comprising a plurality of detector elements each of said detector elements being a segment of the ring and the radial interfaces between detector elements or segments in adjacent annular rings are out of phase, to enable discrimination of the shapes of particles passing through the illuminating beam on the basis of the light scattering; and
    (v) a data processor adapted to capture and process the signals from the optical detector for each particle traversing the illuminating beam.

2. A detector assembly according to claim 1 wherein the detector array comprises three concentric annular rings of detector elements.

3. A detector assembly according to claim 1 wherein the detector array comprises three concentric annular rings of detector elements.

4. A detector assembly according to claim 1 wherein the innermost annular ring comprises a single detector and the other annular ring or rings each consist of a plurality of detector elements.

5. A detector assembly according to claim 1 wherein the optical detector comprises three annular rings and the two outermost rings are divided into 16 segments or elements.

6. A detector assembly as according to claim 1 wherein the annular rings of detector elements in the optical detector are substantially circular.

7. A detector assembly according to claim 1 wherein the data processing means incorporates a pattern classifier.

8. A detector assembly according to claim 7 wherein the pattern classifier comprises a neural network.

9. A detector assembly according to claim 8 wherein the neural network is a radial basis function neural network.

10. An optical detector suitable for using a detector assembly that is useable for optical detection of airborne fibers, said optical detector comprising:
    a photodiode array consisting of a central opaque area surrounded by two or more annular rings of detector elements of which rings at least two consist of a plurality of detector elements each element being a segment of the ring to enable discrimination of particle shape on the basis of the light scattering and wherein the radial interfaces between detector elements or segments in adjacent annular rings are out of phase.

11. An optical detector according to claim 10 wherein the innermost annular ring comprises a single detector and the subsequent annular ring or rings each consists of a plurality of detector elements.

12. An optical detector according to claim 10 wherein the optical detector comprises 3 annular rings and the 2 outermost rings are divided into 16 segments or elements.

13. An optical detector according to claim 10 wherein the annular said annular rings are substantially circular.

14. An optical detector according to claim 10 wherein said detector comprises a 33 element detector array chip having an outer annular ring that comprises 16 elements and an intermediate annular ring that comprises 16 elements, and an inner annular ring that comprises 1 element.

* * * * *